United States Patent [19]

Parzuchowski et al.

[11] Patent Number: 5,698,787
[45] Date of Patent: Dec. 16, 1997

[54] PORTABLE LASER/ULTRASONIC METHOD FOR NONDESTRUCTIVE INSPECTION OF COMPLEX STRUCTURES

[75] Inventors: Halina M. Parzuchowski, Ballwin; Mark K. Reighard, O'Fallon; Kevin G. Kintz, St. Charles, all of Mo.

[73] Assignee: McDonnell Douglas Corporation, St. Louis, Mo.

[21] Appl. No.: 420,501

[22] Filed: Apr. 12, 1995

[51] Int. Cl.$^6$ .................................................. G01N 29/00
[52] U.S. Cl. .............................. 73/643; 73/588; 73/583; 73/635; 73/633; 73/640
[58] Field of Search .......................... 73/643, 588, 583, 73/655, 657, 600, 635, 633, 640, 641; 356/429, 430, 431, 241, 237

[56] References Cited

U.S. PATENT DOCUMENTS

| | | | |
|---|---|---|---|
| 4,121,470 | 10/1978 | Kaule | 73/643 |
| 4,144,767 | 3/1979 | Kaule et al. | 73/643 |
| 4,169,662 | 10/1979 | Kaule et al. | 350/358 |
| 4,338,822 | 7/1982 | Yamaguchi et al. | 73/643 |
| 4,379,409 | 4/1983 | Primbsch et al. | 73/643 |
| 4,407,293 | 10/1983 | Suarez, Jr. et al. | 128/660 |
| 4,430,897 | 2/1984 | Quate | 73/606 |
| 4,470,122 | 9/1984 | Sarr | 364/559 |
| 4,484,820 | 11/1984 | Rosencwaig | 374/6 |
| 4,567,769 | 2/1986 | Barkhoudarian | 73/643 |
| 4,581,939 | 4/1986 | Takahashi | 73/643 |
| 4,622,853 | 11/1986 | Leugers | 73/597 |
| 4,674,332 | 6/1987 | Pace et al. | 73/597 |
| 4,758,691 | 7/1988 | De Bruyne | 178/19 |
| 4,774,842 | 10/1988 | Kollar et al. | 73/640 |
| 4,801,799 | 1/1989 | Tromberg et al. | 250/227 |
| 4,807,476 | 2/1989 | Cook et al. | 73/620 |
| 4,848,159 | 7/1989 | Kennedy et al. | 73/641 |
| 4,928,527 | 5/1990 | Burger et al. | 73/657 |
| 5,070,733 | 12/1991 | Nagata et al. | 73/602 |
| 5,099,693 | 3/1992 | Payne et al. | 73/632 |

OTHER PUBLICATIONS

MAUS III® Mobile AUtomated Scanner III Technical Description; Jul. 15, 1993.

*Primary Examiner*—Hezron E. Williams
*Assistant Examiner*—Richard A. Moller
*Attorney, Agent, or Firm*—Bryan Cave LLP

[57] ABSTRACT

A method and apparatus for non-destructive inspection of complex structures employs a portable laser based ultrasonic transducer 600 output to rapidly detect and size flaws in such structures, including the radii of composites, laminates, and complex skin/substructure assemblies, such as airplane wings. A fiber optic delivery system 610A is employed with the laser based ultrasonic transducer 600 and a thermoelastic medium to rapidly and accurately access the radii of complex structures in the field without the need for liquid or gel couplants, with the thermoelastic expansion of the test piece 680 producing mechanical stresses that initiate detectable sound waves regardless of the angle of the laser based ultrasonic transducer 600 output with respect to the test piece 680. A MAUS III scanning device may be employed to detect these sound waves and provide accurate information as to the detected flaws.

19 Claims, 9 Drawing Sheets

Delamination in Radius

PORTABLE LASER/ULTRASONIC METHOD FOR NONDESTRUCTIVE INSPECTION OF COMPLEX STRUCTURES

BACKGROUND OF THE INVENTION

The present invention relates in general to ultrasonic inspection and, more particularly, to the use of portable, hand-held, laser based ultrasonic transducers to rapidly detect and size flaws in complex structures, particularly including the radii of composites, laminates, and complex skin/substructure assemblies.

An ever-increasing number of aircraft and aerospace parts are being constructed from so-called, co-cured, bonded, laminated layers of high strength, composite material because parts so fabricated are lighter and easier to manufacture (especially where the part includes compound curves) than comparable metal parts. These parts are typically formed by co-curing or consolidating multiple layers of, e.g., graphite/epoxy, fiber-reinforced resins using carbon (CRC), glass (GRC), boron, aramid fibers, or other fiber/resin composite materials, into a laminate of desired configuration.

Figure 1:
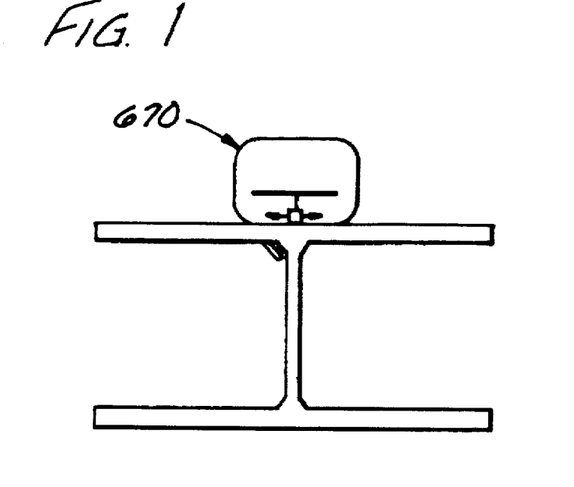
FIG. 1 is a schematic sectional representation of a preferred embodiment of an apparatus of the present invention, with a fiber optic guide shoe assembly designed to direct laser energy into the radius area of one of the joints of an "T" configuration composite structure, and to be received by a receiving transducer.
Figure 2:
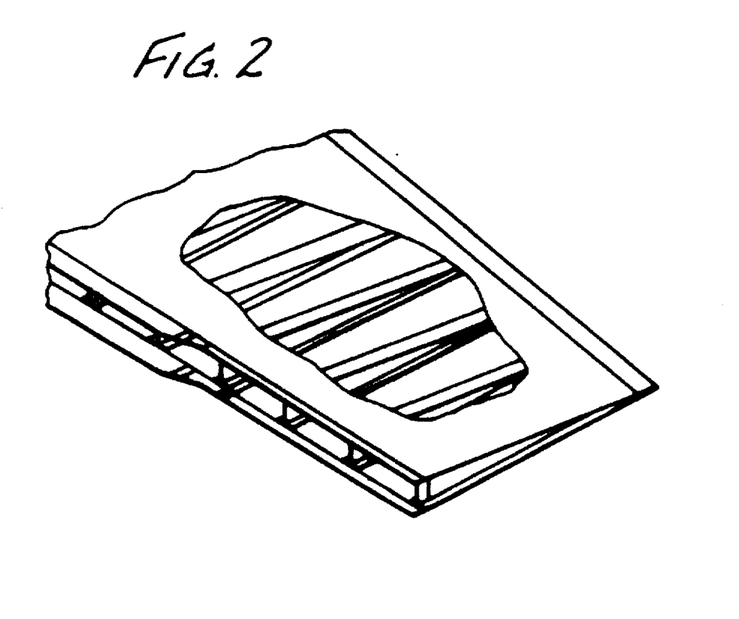
FIG. 2 is a partial sectional representation of a portion of an airplane wing utilizing the "T" configuration junctures between skin and stiffeners.
Figure 3:
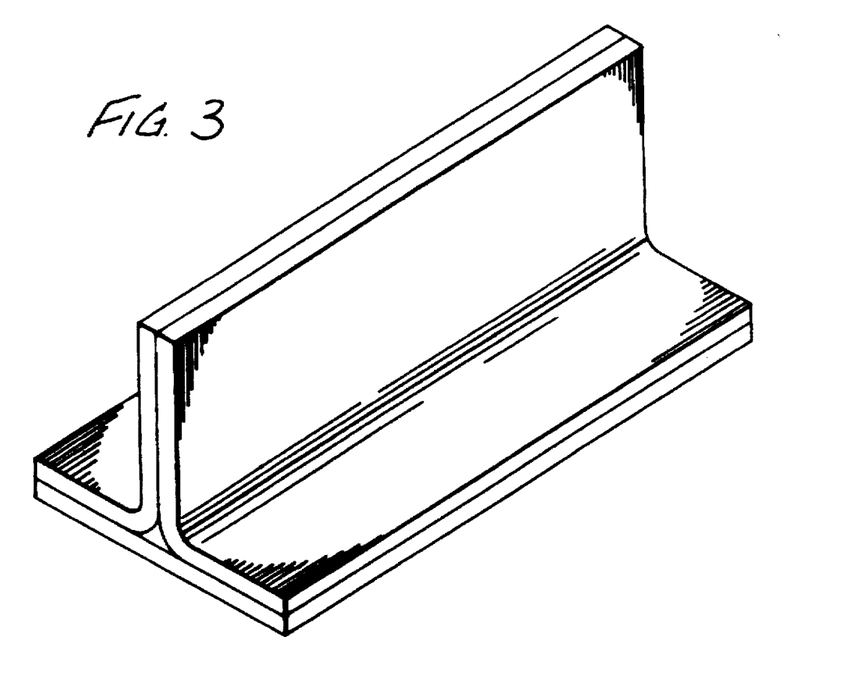
FIG. 3 is a perspective view of a blade-stiffened "T" juncture laminate structure.
Figure 4:
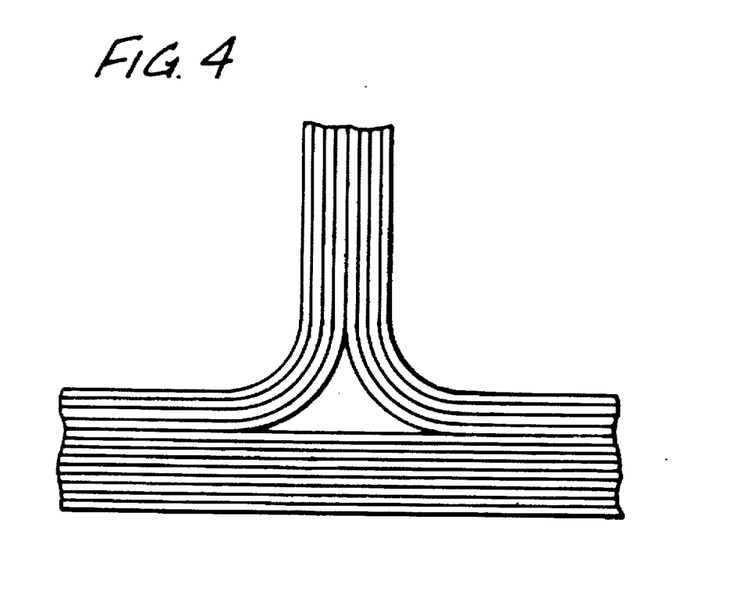
FIG. 4 is a pictorial sectional representation of the blade-skin intersection of the structure of FIG. 3.

As technology for manufacturing such co-cured composite, laminate structures has advanced, the complexity of these structures has also advanced, resulting in the fabrication of large-scale, laminated, composite panels which have integral stiffeners (e.g. ribs) joined to the panel skins (see the sample wing structure of FIG. 2), characterized by complex juncture geometries, e.g "hat," "T," "I," "L," or "Z" cross-sectional configurations (see FIG. 1 for an example of an "I" structure, and FIG. 3 for an example of a "T" structure). In the juncture regions between the stiffeners and skins of such co-cured structures, the stiffeners are created and joined to the skins usually by structuring layers or plies of composite material to meet at opposite sides of a bend (e.g. ninety degrees; see FIG. 4) on one side of the panel skins, usually forming a smooth curve. As a consequence of such construction, there also typically exists a cross-sectionally triangular cavity formed by the intersection of the skin and stiffener plies, such cavity being filled with fiber free resin, forming a so-called fillet.

The fillet area, i.e. the radius areas of the curved juncture of the co-cured stiffeners to skins, is a critical area where any delamination of, or other flaw in, such co-cured structures can result in a significant loss of strength for the entire co-cured structure. Possible defects besides delamination include pores, inclusions, cracks and gaps, also transverse to the main directions of the plies, which are produced by bonding faults, by insufficient resin, incomplete curing or lack of inter-layer adhesion. Accordingly, there is an important need for suitable inspection methods able to detect flaws in these critical juncture areas.

There moreover is a need for suitable inspection methods that not only can be used to test for such flaws during the manufacture of such co-cured structures, but also can be used to field-test for such flaws after such co-cured structures are installed and have been in operation, e.g. as part of a wing structure on an aircraft.

Although the general concept of laser ultrasonic inspection is well-known, such as described in Kaule U.S. Pat. No. 4,121,470; Kaule et al. U.S. Pat. No. 4,144,767; Kaule et al. U.S. Pat. No. 4,169,662; Yamaguchi et al. U.S. Pat. No. 4,338,822; Primbsch et al. U.S. Pat. No. 4,379,409; Quate U.S. Pat. No. 4,430,897; Rosencwaig U.S. Pat. No. 4,484,820; Barkhoudarian U.S. Pat. No. 4,567,769; Takahashi U.S. Pat. No. 4,581,939; and Nagata et al. U.S. Pat. No. 5,070,733, as well as, see also generally, Krautkramer, J. et al., "Ultrasonic Testing of Materials," 4th Ed. (1990), pp. 142-145, none of the foregoing methods and apparatuses is concerned with the peculiar problems of ultrasonic inspections which are present in the important juncture area of modern, co-cured composite structures. As such, there is no disclosure or suggestion in the prior art of how to effectively utilize laser ultrasonic inspection in such critical juncture areas to accurately, efficiently and rapidly accomplish detection of flaws in such complex structures as airplane wings despite the importance of such detection.

The difficulty with such inspections is well recognized in the prior art, such as described in U.S. Pat. No. 4,848,159, to Kennedy et al., which discusses the difficulty involved in attempting to employ nondestructive, ultrasonic inspection in these critical juncture areas of laminates which stems, in part, from the laminates themselves, and the fact that the flaws in composite or other laminate materials tend to follow the direction of the plies or laminates, as well as the fact that the laminates themselves tend to act as waveguides so that there is little predictability concerning the direction that ultrasonic energy will follow.

These difficulties are even more pronounced in the juncture areas of these laminate structures, owing to the curvature of the laminates and the nature of the fillet or juncture areas, where flaws or voids of many different shapes and orientations are possible. However, although these problems are recognized in the prior art, and discussed in U.S. Pat. No 4,848,159, there is no teaching or suggestion of using lasers as an inspection tool in such areas in order to facilitate accurate, efficient, and rapid inspection of these composite, juncture areas.

Another prior art approach for ultrasonic testing of laminates, compound materials and composites is disclosed in Krautkramer in "Ultrasonic Testing of Materials," 4th Ed. (1990), pp. 473-474, which discloses that the typical prior art choice has been to use "large installations with mechanized scanning and full immersion techniques, or water-jet coupling with either vertical or horizontal jet directions." See also Krautkramer, chapter 15.5, "Coupling Through Intermediate Layers, via Watergaps and by the Immersion Method," at pp. 274-276, also noting that the echo method may be useful, but only with thin test pieces. Krautkramer further discloses that with curved complicated surfaces, water-jet (i.e. "squirter") probes, which are not as beneficial as the method of the present invention, are typically used.

While these prior art techniques may be useful during the manufacture of composite or other laminated structures, in connection with testing of the large skin areas, these techniques, which require liquid or gel couplant to operate, are impractical or undesirable for field use, i.e. for a structure already assembled and in service, e.g. an airplane wing. In the first instance, these juncture areas, especially when the structures are already in use in the field, are frequently difficult to access. Specifically, in-field, service inspections of many radius areas, in particular, is not possible due to the inability to insert the traditional hardware through the relatively small access holes to reach internal radius regions. Secondly, even where, arquendo, access is sufficient for such traditional hardware to be inserted internally into the structure, it may be undesirable to immerse the structure or otherwise insert liquid or gel couplant into the aircraft structure to enable the types of inspection discussed, by way of example in Krautkramer, as suitable for laminates, since the couplant/liquid may cause contamination and ultimately lead to material corrosion and structural failure. Moreover, the use of couplant/liquid requires a method of recovery of such liquid, again making it particularly undesirable for field use.

The radii area of the juncture areas of these composite structures, is particularly ill-suited to effective inspection by conventional prior art techniques noted by Krautkramer, as recognized by U.S. Pat. No. 4,848,159, which discloses a technique specifically designed to detect flaws in the radii area of composite laminates. However, the technique disclosed in U.S. Pat. No. 4,848,159, contemplates the incorporation of transmitting transducers that still utilize a liquid to provide ultrasound coupling between the transducers and the test piece (Col. 2, lines 44–47), which is less desirable than the present invention which does not use any liquid or gel couplant with the transmitting transducer.

These disadvantages of the prior art are overcome by the present invention which has among its objects, to provide for a method and apparatus of ultrasonic inspection comprising the use of portable, laser based ultrasonic transducers to detect and size flaws in complex structures, particularly including the radii of composites and laminates, and further which is suitable for being used to inspect structures which are in use in the field. These and other objects and advantages of the invention will be apparent from the following description of the preferred embodiments thereof.

SUMMARY OF THE INVENTION

The method and apparatus of the present invention provides a means to effectively inspect complex curved structures that are in-service and which thus may have limited accessibility without the need for liquid or gel couplant to be inserted into the structure to enable inspection. In accordance with the apparatus of the invention, there is at least one laser based ultrasonic transmitting, transducer means coupled to means to deliver at least one, movable, incident laser beam to a test object so as to generate ultrasonic energy output for through transmission of the ultrasonic energy output in the test article, such transmission representing a characteristic of the internal composition of the test object; at least one movable, ultrasonic, receiving, transducer means mounted on the test object opposite the movable incident laser beam, so as to receive the through transmission of ultrasonic energy output from the laser beam in the test article, the receiving transducer means further producing an output representing the transmission of ultrasonic energy generated by the laser beam in the test object; harmonic moving means for automatically and harmonically moving the receiving transducer means relative to the movement of the movable incident laser beam; and means for detecting and displaying the position coordinates of any flaw in the test object which is identified as a result of a variation in the ultrasonic energy output transmitted through the test piece. The means for detecting and displaying the position coordinates of any flaw in the test object themselves preferably comprise positioning means for producing an integrated position output for the transmitting transducer means and the receiving transducer means representing the position coordinates of the harmonically moving transducers relative to the test object; signal collating means for receiving the output of the receiving transducer and of the integrated position output, and for pairing the receiving transducer output with the integrated position output; and indicating means responsive to the signal collating means for indicating the correlative relationship between the receiving transducer output and the integrated position output that have been paired.

The portable, laser based ultrasonic inspection assembly of the invention offers several advantages over prior art inspection systems, particularly for accurately, efficiently and rapidly detecting flaws in complex structures. Many of these advantages relate to the ability of the apparatus of the invention to be readily used in the field for complex structures already in-service, such as aircraft wings. For example, because of the preferred use of a fiber optic laser delivery system which is quite small, it is possible to access the radii of complex structures that are in-service, which have, in the past, been inaccessible to traditional prior art inspection techniques. The apparatus of the invention is further advantageous for inspection of in-service structures, because the preferred fiber optic laser delivery system, unlike other traditional inspection techniques, requires no liquid or gel couplant, enabling radii internal to a structure to be inspected without introducing undesirable liquid couplant into such internal areas.

Yet other advantages of the invention relate specifically to the preferred use of fiber optic laser delivery means which enables the area of ultrasonic wave propagation to be controllably tailored to accurately and rapidly detect much smaller flaws in a laminate radius area than is possible using prior art ultrasonic wave propagation techniques.

Moreover, the use of a fiber optic delivery assembly in the apparatus and method of the present invention minimizes air travel of the laser beam delivered to the test piece, making the use of this invention relatively safer than the use of other delivery techniques. The safety of the fiber optic delivery technique and relatively low laser energy used in the invention enables the apparatus of the invention to be portable, thus permitting the apparatus to be used effectively in-field, e.g., in an aircraft maintenance inspection environment.

Another advantage of the present invention relates to the nature of laser beam ultrasonic propagation which is based upon the heating of a body suddenly ("heat shock"), and the thermoelastic expansion of the test body producing mechanical stresses that initiate sound waves. This thermoelastic expansion of the test piece takes place regardless of whether the angle of the laser beam is normal or not normal to the test piece, as contrasted with prior art methods employing other sources of ultrasonic energy which require that the ultrasonic transmitting transducer be maintained at an angle normal to the inspection surface in order to obtain effective propagation of ultrasonic energy. Because the angle of an incident laser beam relative to the test body surface is unimportant in effectively heating the test body surface and creating ultrasonic energy in the test body in the present invention, the need to maintain a normal angle of incidence between the inspection surface of the test piece and the ultrasonic source is eliminated, offering the advantage of eliminating the need for exact positioning of the ultrasonic transmitting transducer, viz. the laser delivery means without affecting the efficiency or accuracy of the flaw detection. This added flexibility is especially useful in the in-field, inspection of complex structures, such as radii of curved surfaces.

DESCRIPTION OF THE PREFERRED EMBODIMENTS

Figure 5:
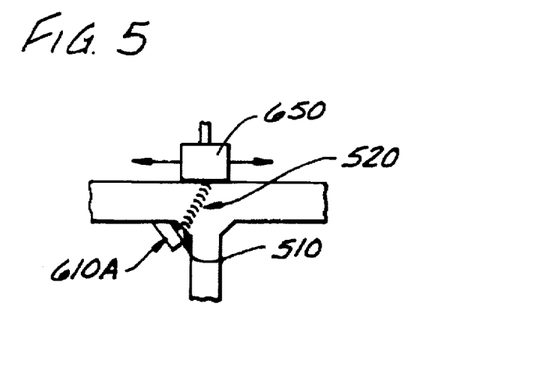
FIG. 5 is another schematic sectional representation of another preferred embodiment of the present invention, with a fiber optic guide shoe assembly designed to direct laser energy, and demonstrating the propagation of ultrasonic waves generated into and through the radius area of one of the joints of a "T" configuration composite structure, and to be received by a receiving transducer.

In a preferred embodiment of the apparatus of the invention, such as the embodiment illustrated by way of example in FIG. 5, laser energy is delivered as an incident laser beam to the radius region 510 formed by a curved juncture of a skin/stiffener, laminate structure, test piece via a small, movable optical fiber guide shoe assembly 610A. Through a conventional thermoelastic mechanism, the incident laser beam on the test piece results in the propagation of ultrasonic energy 520 through the radius region of the structure. At least one receiving transducer 650 is preferably used on the skin, opposite the radius region, which receiving transducer 650 is preferably oscillated across the skin, and which produces a receiving transducer output that is a representation of the ultrasonic energy transmission generated by the incident laser beam. The movable assembly 610A for delivering the incident laser beam and the receiving transducer 650 are preferably coupled by means that permit the two to move harmonically. Moreover, the two are preferably coupled with means for producing an integrated position output representing the position coordinates of the harmonically moving laser ultrasonic energy source assembly 610A and the receiving transducer 650, relative to the test object. There are also preferably signal collating means (not shown) for receiving the integrated position output and the receiving transducer 650 output, and indicating means (not shown) responsive to the signal collating means (not shown) for indicating the correlative relationship between the receiving transducer 650 output and the integrated position output that have been paired.

In the most preferred embodiment, the present invention employs a positioning, detection and scanning display means (not shown) such as a modified version of the commercially available McDonnell Douglas Corporation Mobile Automated Scanner (MAUS III®), a version of which is described, by way of example, in Kollar et al. U.S. Pat. No. 4,774,842, and which is incorporated herein by reference.

Figure 6:
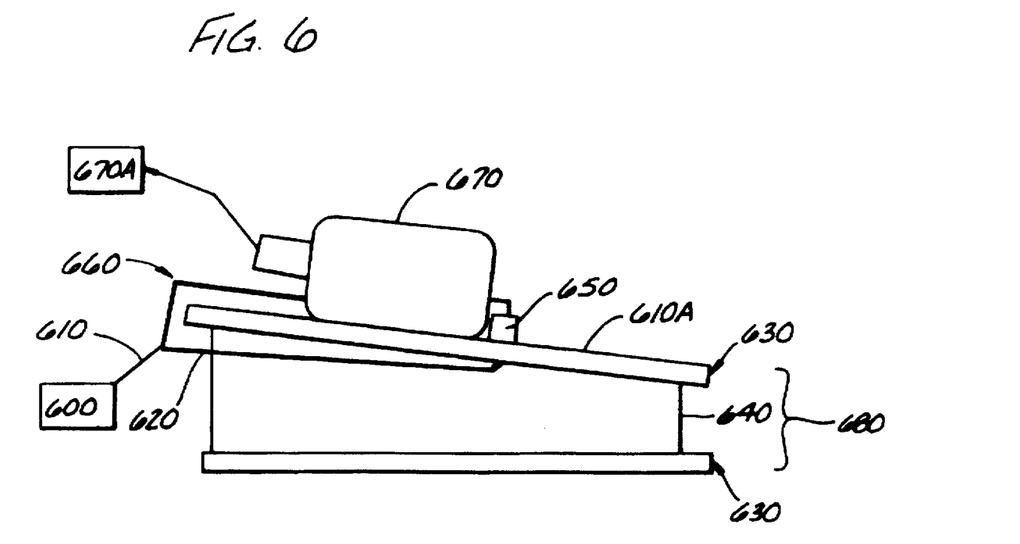
FIG. 6 is another schematic representation, in a side sectional view, of an apparatus of the invention being used to inspect a tapered structure similar to that of FIG. 1.

Another preferred embodiment of the apparatus of the present invention is illustrated schematically in FIG. 6. The apparatus shown in FIG. 6 preferably includes at least one laser based ultrasonic transmitting, transducer 600 connected to a movable assembly 610A to deliver a laser beam to the test object 680 so as to generate ultrasonic energy output for through transmission of the ultrasonic energy output in the test article 680, such transmission representing a characteristic of the internal composition of the test object. The laser based ultrasonic transducer 600, in turn, preferably comprises a pulsed Nd:YAG laser (1064 nanometer wavelength) connected to a laser-suitable optic fiber 610 that, in turn, is threaded through a guide arm 620 in order to transmit incident laser energy to an optical fiber guide shoe assembly 610A in the radius area of the test object 680 that is formed by the intersection of a co-cured composite structure comprising two skins 630 joined by a stiffener 640. As shown and preferred in FIG. 6, the apparatus of the present invention includes at least one movable, ultrasonic, receiving, transducer such as a piezoelectric ultrasonic receiving transducer 650, mounted on the surface skin of the test object opposite the delivery location of the incident laser energy (through the movable assembly 610A), so as to receive the through transmission of ultrasonic energy output from the laser based ultrasonic transducer 600 in the test object 680. The receiving transducer 650 itself preferably produces an output representing the ultrasonic transmission generated in the test piece by the incident laser beam. The apparatus of FIG. 6 further preferably includes harmonic moving means 660 for automatically and harmonically moving the movable incident laser beam assembly 610A relative to the movement of the receiving transducer 650. Such harmonic moving means are shown in FIG. 6 as comprising, by way of example, a rigid, physical connection 660 between the laser based ultrasonic transducer 600, optical fiber guide arm 620 with related movable guide shoe assembly 610A, and the piezoelectric receiving transducer 650. As further shown and preferred in FIG. 6, a positioning means 670A for producing an integrated position output for the incident laser beam assembly 610A and the receiving transducer 650 representing the position coordinates of the harmonically moving incident laser beam assembly 610A and receiving transducer 650 relative to the test object, is illustrated in FIG. 6 as an integral part of the MAUS III® scanning device 670 and 670A, such as described in U.S. Pat. No. 4,774,842. A signal collating means 670A is shown schematically, for receiving the output of the receiving transducer 650 and of the integrated position output, and for pairing the receiving transducer 650 output with the integrated position output, is also preferably provided as an integral part of the MAUS III scanning device 670 and 670A. In addition, indicating means 670A responsive to the signal collating means 670A for indicating the correlative relationship between the receiving transducer 650 output and the integrated position output that have been paired, is also preferably provided as an integral part of the MAUS III scanning device 670 and 670A.

In the preferred embodiment illustrated in FIG. 5, laser energy is preferably delivered to the radius region via a small optical fiber delivery assembly 610A described above. While the optical fiber laser beam delivery assembly 610A is also shown by way of example in the preferred embodiment illustrated in FIG. 6, the invention is intended to encompass any means to deliver incident laser energy to a desired location on a test article. As a further example only, and not intended as a limitation on the scope of the invention, other suitable means by which the incident laser pulse may be delivered to the test article, may include by way of example, appropriately angled mirrors which will serve to direct and propagate the laser pulse to a desired delivery location.

As further shown and preferred in FIG. 5, the laser energy incident upon the test piece laminate structure results in the propagation of ultrasonic energy 520 through the radius region of the structure, by means of a conventional thermoelastic mechanism. At least one receiving transducer 650 is preferably positioned on the skin of the laminate structure, opposite the incident laser energy output, with the receiving transducer 650 being preferably oscillated across the skin of the structure and producing a receiving transducer output that is a representation of the ultrasonic transmission from the incident laser beam.

The means for delivering the movable, incident laser beam, preferably shown as the assembly 610A, and the receiving transducer 650 are preferably coupled by means that permit the two to move harmonically, so that the receiving transducer 650 is capable of and will receive the transmission generated by the incident laser beam. While, as previously mentioned, such harmonic moving means are shown as a rigid connecting member 660 in the preferred embodiment illustrated in FIG. 6, the invention is intended to encompass any means to harmonically move the incident, laser based ultrasonic transmission, with the receiving transducer 650 being capable of receiving such ultrasonic transmission. As a further example only, and not intended as a limitation on the scope of the invention, other suitable means by which the laser pulse may be moved harmonically with the receiving transducer 650, may include a magnetized shoe to hold a laser-transmitting optic fiber, which shoe magnetically and automatically follows a magnet companion piece in the housing carrying the receiving transducer. It is part of a preferred embodiment of the invention as illustrated in FIGS. 1 and 6 to couple the receiving transducer 650 and laser delivery assembly 610A with means for producing an integrated position output representing the position coordinates of the harmonically moving incident laser beam assembly 610A and receiving transducer 650 relative to the test object. There are, moreover, signal collating means 670A for receiving the integrated position output and the receiving transducer output, and indicating means 670A responsive to the signal collating means for indicating the correlative relationship between the receiving transducer output and the integrated position output that have been paired. As previously mentioned, preferably the position output means 670A, signal collating means 670A, and indicating means 670A are all integral parts of the MAUS III scanning device 670 and 670A.

Figure 7:
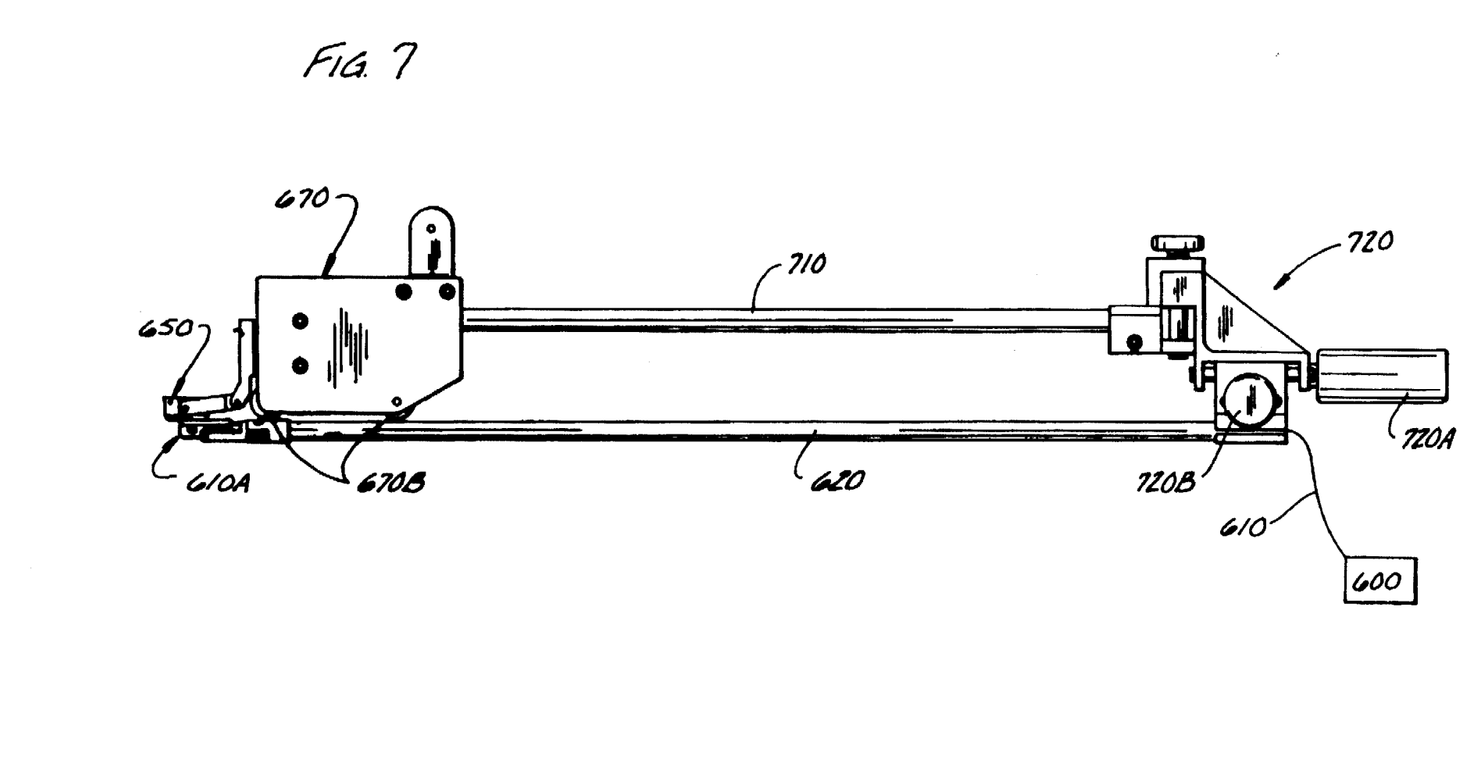
FIG. 7 is a plan view of a preferred apparatus according to the present invention.

FIG. 7 is a plan view of the principal hardware of another preferred embodiment of the apparatus according to the present invention. Principally, FIG. 7 shows in greater detail the harmonic moving means which connect and coordinate the movement of the means for delivering the movable laser beam, and the piezoelectric receiving transducer. This embodiment specifically comprises a MAUS III scan head 670 incorporating oscillating piezoelectric, receiving transducers 650. The MAUS III scan head 670 is preferably connected by a standard connector cable (not shown in FIG. 7) of a desired length to the rest of the MAUS III detection/display equipment 670A. The MAUS III scan head 670 is preferably connected by a connecting support rod 710 to a grip handle unit 720 having a handle 720A. The grip handle unit 720, in turn, is preferably connected to a guide arm 620 which itself serves to guide an optical fiber 610 threaded therethrough. The optical fiber 610 is preferably connected to a laser based ultrasonic transducer 600. The optical fiber 610 preferably transmits incident laser energy to the optical fiber guide shoe assembly 610A, that is secured in a position opposite the oscillating piezoelectric receiving transducer 650, by means of the same guide arm 620 that supports the optical fiber 610. A test article is preferably introduced between the guide shoe assembly 610A which delivers an incident laser beam and the receiving transducer 650 opposite the guide shoe assembly 610A. Preferably, as the MAUS III scan head 670 and piezoelectric receiving transducer 650 ride on top of the test piece via wheels 670B in the MAUS III scan head 670 and wheels 720B in the grip handle unit 720, the optical fiber guide shoe assembly 610A automatically rides on the opposite side of the test piece in the radii area of a joint on a test piece opposite the piezoelectric receiving transducer 650, automatically following the receiving transducer 650, due to their mutual connection with the grip handle unit 720. The length of the connecting support rod 710 and the guide arm 620 may preferably be lengthened of course to accommodate the inspection of test pieces of greater length than illustrated. The preferred embodiment shown in FIG. 7 is particularly well-suited to inspection of such structures as exemplified in FIGS. 2 and 6.

Figure 8:
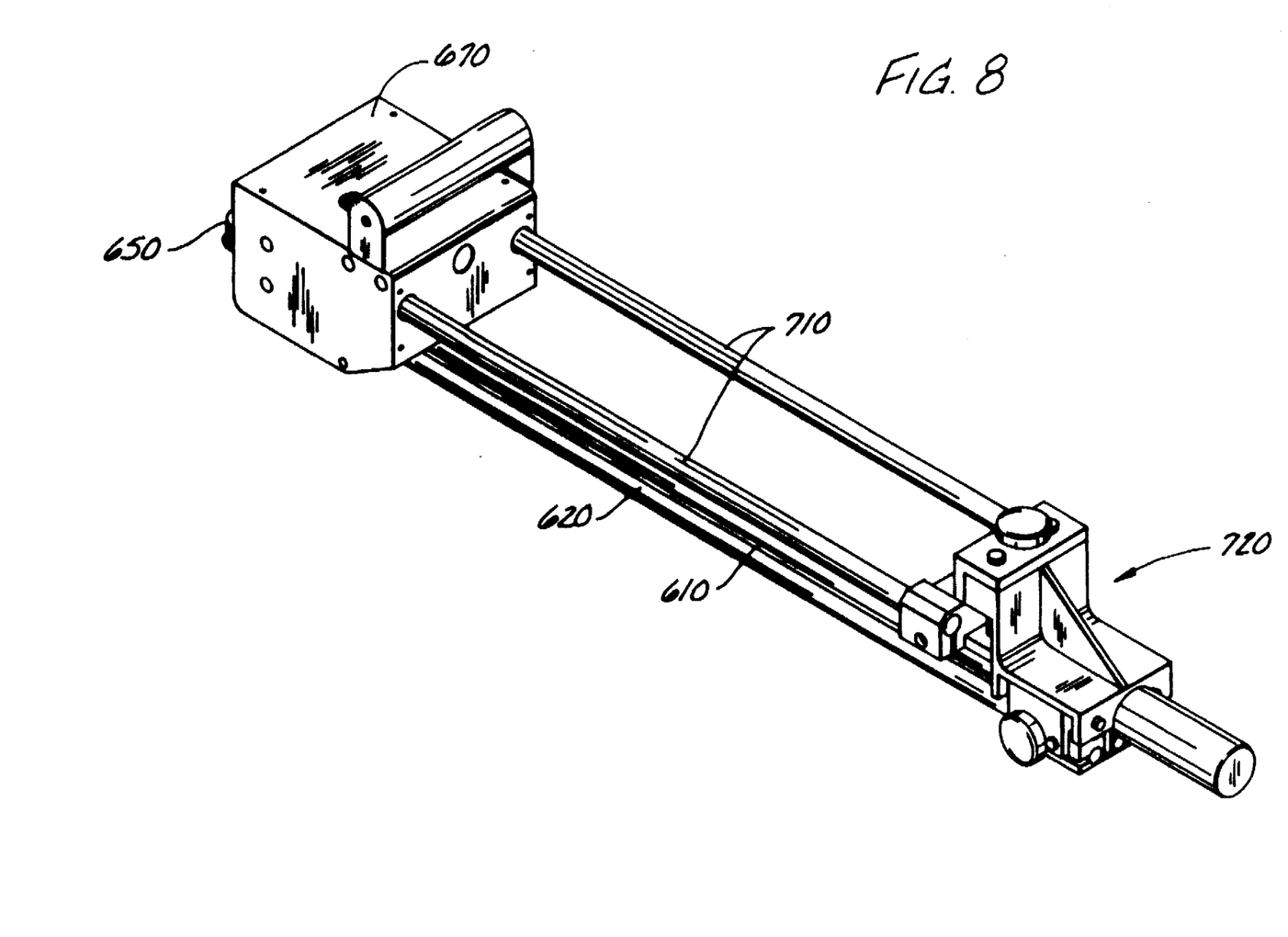
FIG. 8 is a perspective view of the preferred apparatus of FIG. 7.

FIG. 8 is a perspective view of the preferred apparatus of FIG. 7, showing two connecting support rods 710 connecting the MAUS III scan head 670 to the grip handle unit 720. It is contemplated by the present invention that, if desired, there may be two guide arms 620 for two optic fibers 610, which can deliver laser energy simultaneously to two guide shoes assemblies 610A on opposite sides of a "T" joint (e.g. see FIG. 5), thereby providing a potential two-fold decrease in inspection time of the radius area of a given co-cured, composite joint.

Figure 9:
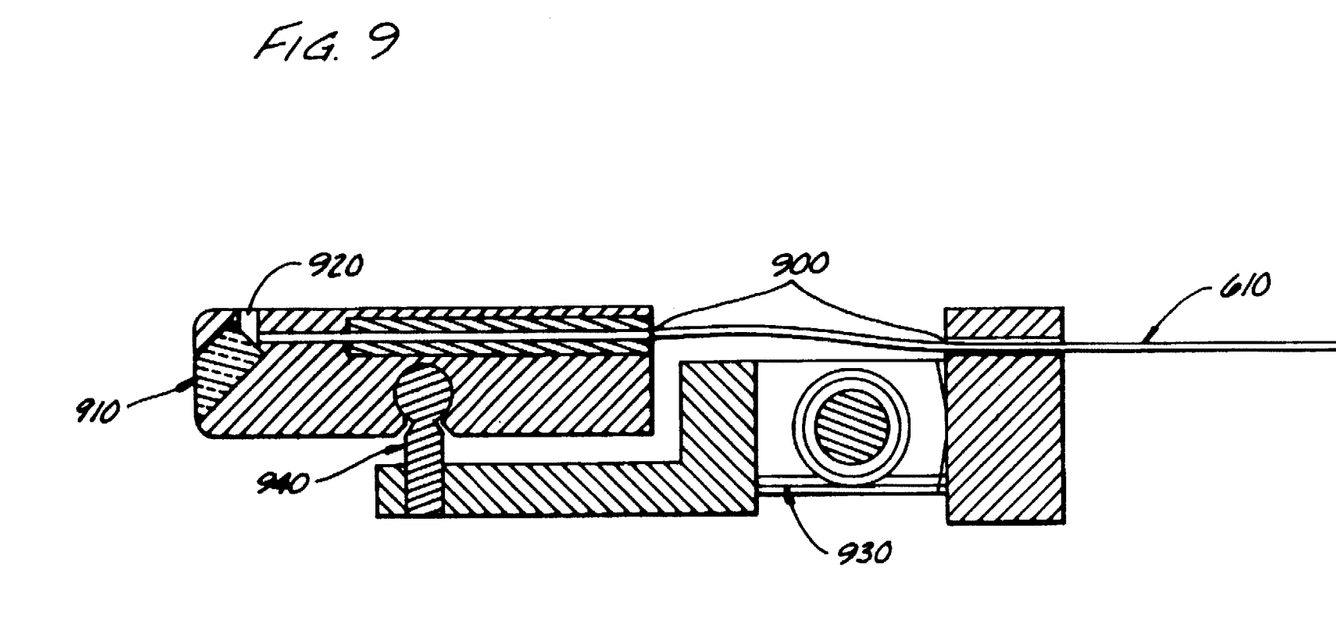
FIG. 9 is a side sectional view of the preferred fiber optic laser guide shoe assembly of FIG. 7.

FIG. 9 is a side sectional view of the preferred fiber optic laser guide shoe assembly 610A for use with the preferred apparatus of FIG. 7! The shoe assembly 610A is connected to the optic fiber guide arm 620 (not shown in FIG. 9), the optic fiber 610 passing through apertures 900 and terminating in front of mirror 910. The laser light passing through the optic fiber 610 will strike the mirror 910, set in this preferred embodiment at a 45° angle, so as to reflect the laser light at an angle 90° to the laser light incoming through the optic fiber 610, so that the reflected light will preferably pass through aperture 920 in order to strike the surface of a test piece above the guide shoe assembly 610A. So that the guide shoe assembly 610A may better be able to stay in position along a radius area of a "T" type joint (e.g. as illustrated in FIG. 2), the preferred embodiment of the assembly 610A here shown preferably includes a torsion spring 930 tending to urge the assembly into the radius area, and a swivel ball 940 permitting the assembly to pivot slightly in response to any curvature in the structure of the radius area.

Figure 10:
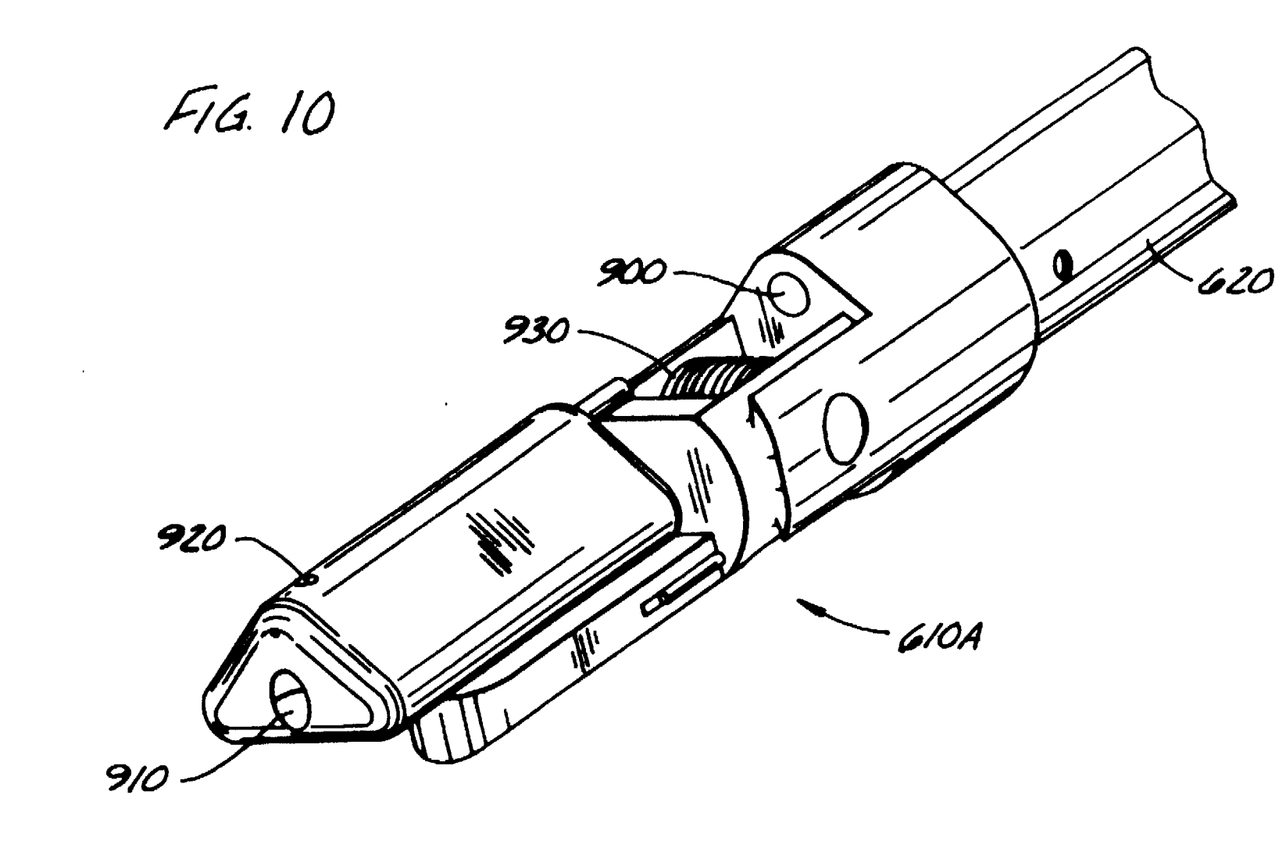
FIG. 10 is a perspective view of a preferred fiber optic laser guide shoe assembly of FIG. 9 for use with the preferred apparatus of FIG. 7.

FIG. 10 is a perspective view of the preferred fiber optic laser guide shoe assembly 610A of FIG. 9 for use with the preferred apparatus of FIG. 7, showing the guide shoe assembly 610A connected to the guide arm 620. Moreover, FIG. 10 shows that a cross-section of the preferred shoe assembly 610A containing the mirror 910 may, generally, preferably be triangular, so as to engage better with the radius area of a "T" type joint.

Figure 11:
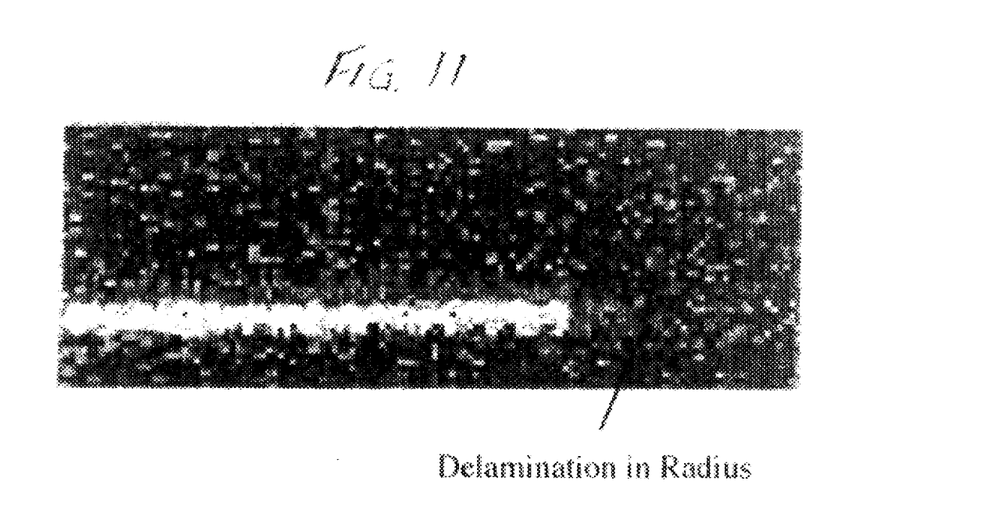
FIG. 11 is a photograph of a C-scan image based on an inspection of a test piece, showing a delamination in the radius of the juncture of a composite skin to a "T" stiffener.

The MAUS III scanning equipment that is used in a preferred embodiment of the invention preferably produces conventional C-scan format images. FIG. 11 is a example of a photograph of a typical C-scan image based on an inspection of a test piece using a prototype of the invention employing a Nd:YAG laser, by way of example, coupled to a MAUS III scanner. This C-scan shows a delamination in the radius of the test piece, illustrated in the scan at area 1100. Signal loss indicates the presence of a radius flaw, and in the photograph of FIG. 11, the white transmission band across most of the C-scan indicates that ultrasonic energy is being transmitted through the radius region, thus signifying an absence of flaws. However, the disappearance of this transmission band towards the right of FIG. 11, at area 1100, coincided with a delamination in the radius region of the juncture between the skin and the stiffener of this co-cured composite test piece.

Figure 12:
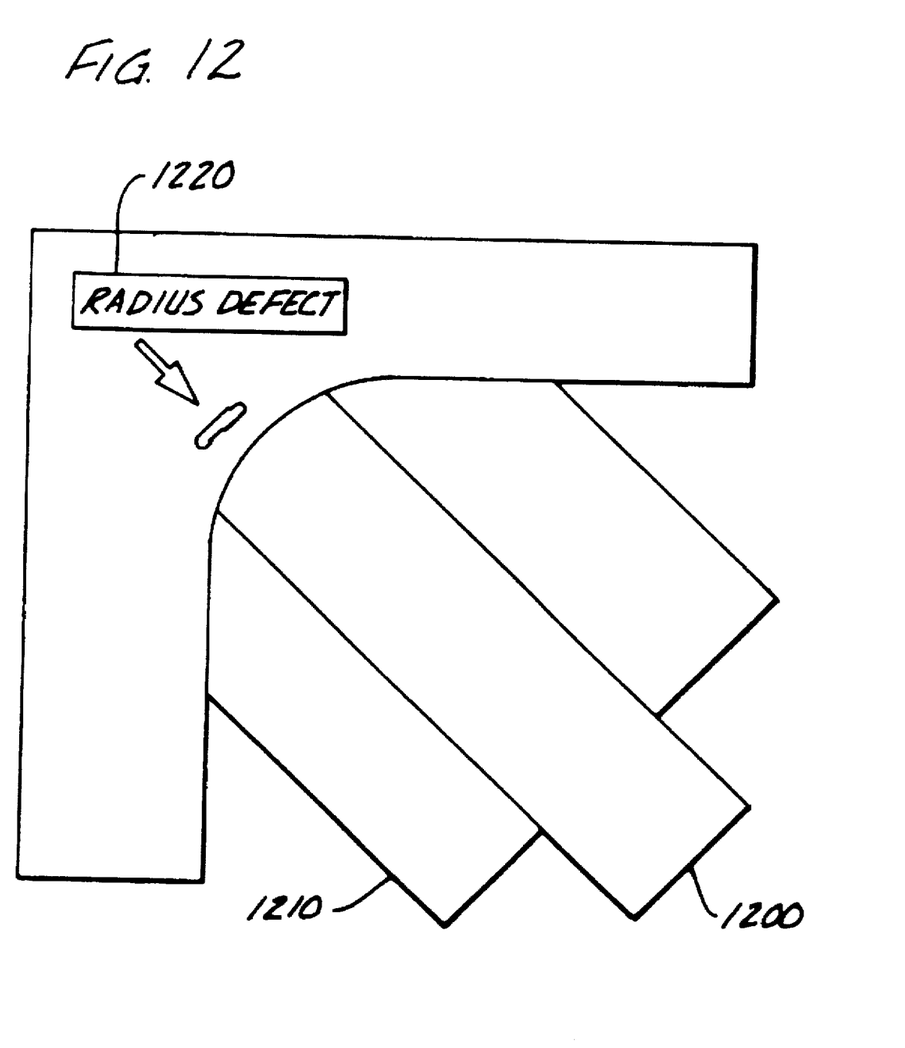
FIG. 12 is a schematic comparison of the difference between the area of ultrasonic wave propagation that can be generated by a laser source in accordance with the present invention, and the area of ultrasonic wave propagation typically generated by a conventional prior art squirter apparatus.

It has been noted that one of the advantages of utilizing laser energy in the present invention is that laser energy permits a smaller area on the test piece to be insonified, thereby providing the potential to detect relatively small defects in the radius area of a co-cured composite area. This ability to insonify a smaller area of a test piece is illustrated in FIG. 12, which presents a schematic comparison of the difference between the area 1200 of ultrasonic wave propagation that can be generated by a laser source as contemplated within the invention, and the area 1210 of ultrasonic wave propagation generated by a typical prior art water-jet, squirter apparatus. The exemplary, relatively small defect 1220 shown in FIG. 12 may not be detected by the relatively wide wave propagation generated by a typical prior art squirter apparatus, but can readily be detected by the narrower wave propagation of the laser used in accordance with the present invention.

The incident laser beam, and the consequent area of wave propagation on the surface of a test piece, may be manipulated by the choice of optical fiber, as well as the laser source. Typically useful optic fibers for use in the invention will have a diameter of from about 100 to 1000 microns. In particular, an optic fiber having a diameter of from about 250 to 750 microns is preferred. Utilizing preferred optic fibers, the diameter of the spot created on the test piece by an incident laser is preferably between about 200 to 300 micrometers, but the spot may be as large as 1 mm in diameter. Of course, the actual diameter of the spot created by an incident laser that may be successfully used in the invention may be varied depending on the desired degree of sensitivity of detection, i.e. for how small a defect one wishes to test.

A preferred laser source is a Nd:YAG laser which has been utilized in the present invention with a 1.06 nm pulse, Flashlamp Pumped, A/O Modulated (100 nanosecond pulsewidth), 5 mJ Maximum Output. Other suitable lasers of course may be chosen, including, e.g., any Q-switched laser with comparable peak power, so long as it produces through transmission ultrasonic energy output in a desired test object.

A preferred piezoelectric receiving transducer is a 5 Mhz receiver transducer. Another preferred receiving transducer is a 2.5 Mhz transducer. Other suitable receiving transducers of course may be chosen. See Krautkramer, J. et al., "Ultrasonic Testing of Materials," 4th Ed. (1990), chapter 8, pp. 141–159.

In summary, the present apparatus provides a useful means by which to conduct a nondestructive inspection of the radius region of a joint created in many of today's co-cured composite structures useful in the aerospace industry, particularly in those structures in field use, for which access may be small, or in which the use of a liquid couplant in the interior of the structure is undesirable. Of course, as the use of complex composite structures expands into non-aerospace markets, the methodology associated with the present apparatus may find useful application in assessing the quality of composite structures in automotive, naval/marine, and civil engineering projects (e.g. bridge decks and dams). In addition to conventional resin matrix composites, the present apparatus may find useful application in assessing the quality of other types of composites, such as ceramic and metal matrix composites, or even monolithic materials such as metals, ceramic, and plastics.

As various changes may be made in the preferred embodiments described above without departing from the scope of the present invention, it is intended that the foregoing description should be deemed illustrative rather than limiting.

What is claimed is:

1. An apparatus comprising:

at least one laser based ultrasonic transmitting, transducer means, and movable delivery means for delivering at least one incident, laser based ultrasonic transducer output to a test object so as to generate ultrasonic energy output for through transmission of said ultrasonic energy output in the test object, said laser based ultrasonic transmitting transducer means being connected to said movable delivery means for providing said incident laser based ultrasonic transducer output;

at least one movable, ultrasonic, receiving, transducer means mounted on the test object opposite said incident, laser based ultrasonic transducer output for receiving the through transmission of ultrasonic energy output from said incident, laser based ultrasonic transducer output in said test article, said receiving transducer means further comprising means for oscillating said receiving transducer means opposite said movable laser based ultrasonic transducer output, said receiving transducer means further producing an output representing the ultrasonic transmission through the test object from the laser based ultrasonic transducer output;

harmonic moving means for automatically and harmonically moving the incident laser based ultrasonic transducer output along one side of the test object, correlative to the movement of the receiving transducer means; and means for detecting and displaying the position coordinates of any flaw in the test object which is identified as a result of a variation in the ultrasonic energy output transmitted through the test object.

2. An apparatus according to claim 1 wherein said means to deliver said movable laser based ultrasonic transducer output comprises an optical fiber laser based ultrasonic transducer output delivery assembly.

3. An apparatus according to claim 2 wherein said optical fiber laser based ultrasonic transducer output delivery assembly comprises an optical fiber held in place against the test object by a fiber optic guide shoe.

4. An apparatus according to claim 1 wherein said at least one movable, ultrasonic, receiving, transducer means comprises a piezoelectric receiving transducer.

5. An apparatus according to claim 1 wherein said harmonic moving means comprise a rigid connecting member between said incident laser based ultrasonic transducer output means and said receiving transducer means.

6. A method for nondestructively testing and determining the presence, location, and size of flaws in at least one juncture in a complex structure, comprising the steps of:

- delivering to said at least one juncture at least one movable laser based ultrasonic transducer output from at least one laser based, transmitting transducer means, so as to generate ultrasonic energy output for through transmission of said ultrasonic energy output at said at least one juncture;
- receiving said through transmission of said ultrasonic energy output by using at least one movable, ultrasonic, receiving, transducer means mounted on the complex structure opposite the incident laser based ultrasonic transducer output;
- oscillating said receiving transducer opposite the movable laser based ultrasonic transducer output;
- harmonically moving said movable, ultrasonic receiving transducer means and said movable laser based ultrasonic transducer output along the complex structure; and
- detecting and displaying position coordinates of any flaw in said at least one juncture in a complex juncture, which is identified as a result of a variation in the ultrasonic energy output transmitted through said complex structure, by using means for detecting and displaying such position coordinates.

7. A method according to claim 6 wherein said delivering step comprises the step of delivering said movable laser based ultrasonic transducer output with an optical fiber, laser based ultrasonic transducer output delivery assembly.

8. A method according to claim 7 wherein said delivering step further comprises holding said optical fiber in said delivery assembly in place against said at least one juncture of said complex structure by a fiber optic guide shoe.

9. A method according to claim 6 wherein said receiving step comprises receiving said through transmission with at least one piezoelectric receiving transducer.

10. A method according to claim 6 wherein said harmonically moving step comprises harmonically moving said receiving transducer and said incident laser based ultrasonic transducer output with means comprising a rigid connecting member between the incident laser based ultrasonic transducer output means and the receiving transducer means.

11. A method according to claim 6 wherein said delivering step comprises delivering to a multiplicity of junctures of said complex structure, a multiplicity of movable laser based ultrasonic transducer outputs.

12. An apparatus for nondestructively testing and determining the presence, location, and size of flaws in a test object, comprising:

- at least one laser based ultrasonic transmitting, transducer means; means for delivering a movable, incident, laser based ultrasonic transducer output to said test object so as to generate ultrasonic energy output for through transmission of said ultrasonic energy output in said test object, said through transmission representing a characteristic of the internal composition of said test object;
- at least one movable, ultrasonic, receiving, transducer means mounted on the test object opposite said movable, incident, laser based ultrasonic transducer output so as to receive the through transmission of ultrasonic energy output generated in the test object from said laser based ultrasonic transducer output, said receiving transducer means further comprising means for oscillating said receiving transducer means opposite said movable laser based ultrasonic transducer output, said receiving transducer means further producing an output representing the transmission from the laser based ultrasonic transducer transmitting transducer means;
- harmonic moving means for automatically and harmonically moving said movable, incident, laser based ultrasonic transducer output correlative to the movement of the receiving transducer means;
- positioning means for producing an integrated position output for both the incident laser based ultrasonic transducer output and the receiving transducer means, said integrated position output representing the position coordinates of the harmonically moving laser based ultrasonic transducer output and receiving transducer relative to the test object;
- signal collating means for receiving the output of said receiving transducer and of said integrated position output, and for pairing said receiving transducer output with said integrated position output; and
- indicating means responsive to said signal collating means for indicating the correlative relationship between said receiving transducer output and said integrated position output that have been paired.

13. An apparatus according to claim 12 wherein said laser based ultrasonic transmitting transducer means comprises a Nd:YAG laser.

14. An apparatus according to claim 13 wherein said Nd:YAG laser is connected to means to deliver at least one movable, incident, laser based ultrasonic transducer output that comprise an optical fiber, laser based ultrasonic transducer output delivery assembly.

15. An apparatus according to claim 14 wherein said optical fiber, laser based ultrasonic transducer output delivery assembly comprises an optical fiber held in place against the test object by a fiber optic guide shoe.

16. An apparatus according to claim 12 wherein said at least one movable, ultrasonic, receiving, transducer means comprises a piezoelectric receiving transducer.

17. An apparatus according to claim 12 wherein said harmonic moving means comprise a rigid connecting member between the incident laser based ultrasonic transducer output means and the receiving transducer means.

18. An apparatus for nondestructively testing and determining the presence, location, and size of flaws in at least one juncture in a test object, said at least one juncture having a radius region formed in the test object at the intersection of a skin attached to a stiffener, comprising:

- at least one laser based ultrasonic transmitting, transducer means, and movable delivery means for delivering at least one incident, laser based ultrasonic transducer output to said radius region so as to generate ultrasonic energy output for through transmission of said ultrasonic energy output in the test object, said laser based ultrasonic transmitting transducer means being connected to said movable delivery means for providing said incident laser based ultrasonic transducer output;
- at least one movable, ultrasonic, receiving, transducer means mounted on the skin opposite said incident, laser based ultrasonic transducer output for receiving the through transmission of ultrasonic energy output from said incident, laser based ultrasonic transducer output in said test article, said receiving transducer means further comprising means for oscillating said receiving transducer means opposite said movable laser based ultrasonic transducer output, said receiving transducer means further producing an output representing the ultrasonic transmission through the test object from the laser based ultrasonic transducer output;

harmonic moving means for automatically and harmonically moving the incident laser based ultrasonic transducer output along said radius region of the test object, correlative to the movement of the receiving transducer means; and means for detecting and displaying the position coordinates of any flaw in the test object which is identified as a result of a variation in the ultrasonic energy output transmitted through the test object.

19. A method for nondestructively testing and determining the presence, location, and size of flaws in at least one juncture in a complex structure, said juncture having a radius region formed in the complex structure at the intersection of a skin attached to a stiffener, comprising the steps of:

delivering to said at least one juncture at least one movable laser based ultrasonic transducer output from at least one laser based, transmitting transducer means, so as to generate ultrasonic energy output for through transmission of said ultrasonic energy output at said at least one juncture;

receiving said through transmission of said ultrasonic energy output by using at least one movable, ultrasonic, receiving, transducer means mounted on the skin opposite the incident laser based ultrasonic transducer output;

harmonically moving said movable, ultrasonic receiving transducer means along the skin and said movable laser based ultrasonic transducer output along said radius region; and detecting and displaying position coordinates of any flaw in said at least one juncture in a complex juncture, which is identified as a result of a variation in the ultrasonic energy output transmitted through said complex structure, by using means for detecting and displaying such position coordinates.

* * * * *